US012740958B2

(12) United States Patent
Lizzo et al.

(10) Patent No.: US 12,740,958 B2
(45) **Date of Patent: *Sep. 22, 2026**

(54) COMPOSITIONS AND METHODS USING AT LEAST ONE GLYCINE OR DERIVATIVE THEREOF AND AT LEAST ONE LARGE NEUTRAL AMINO ACID AND/OR CATIONIC AMINO ACID OR PRECURSOR THEREOF

(71) Applicant: SOCIETE DES PRODUITS NESTLE S.A., Vevey (CH)

(72) Inventors: Giulia Lizzo, Echandens (CH); Philipp Gut, Geneva (CH)

(73) Assignee: Societe des Produits Nestle S.A., Vevey (CH)

(*) Notice: Subject to any disclaimer, the term of this patent is extended or adjusted under 35 U.S.C. 154(b) by 581 days.

This patent is subject to a terminal disclaimer.

(21) Appl. No.: 18/256,489

(22) PCT Filed: Dec. 7, 2021

(86) PCT No.: PCT/EP2021/084588

§ 371 (c)(1),
(2) Date: Jun. 8, 2023

(87) PCT Pub. No.: WO2022/122730

PCT Pub. Date: Jun. 16, 2022

(65) Prior Publication Data

US 2024/0100006 A1 Mar. 28, 2024

(30) Foreign Application Priority Data

Dec. 9, 2020 (EP) .................................... 20212799

(51) Int. Cl.

| | |
|---|---|
| ***A61K 31/198*** | (2006.01) |
| ***A61K 31/405*** | (2006.01) |
| ***A61K 31/4172*** | (2006.01) |
| ***A61P 39/06*** | (2006.01) |

(52) U.S. Cl.
CPC .......... *A61K 31/198* (2013.01); *A61K 31/405* (2013.01); *A61K 31/4172* (2013.01); *A61P 39/06* (2018.01)

(58) Field of Classification Search
CPC .................................................... A61K 31/198
See application file for complete search history.

(56) References Cited

U.S. PATENT DOCUMENTS

| | | | | |
|---|---|---|---|---|
| 12,317,914 B2 * | 6/2025 | Feige | .................. | A61K 38/011 |
| 2007/0202203 A1 * | 8/2007 | Amar | .................. | A61K 31/728 514/18.6 |

FOREIGN PATENT DOCUMENTS

| | | |
|---|---|---|
| CN | 103181920 | 7/2013 |
| WO | WO 0249636 * | 6/2002 |
| WO | 2016115632 A1 | 7/2016 |
| WO | 2020064692 | 4/2020 |
| WO | 2020130146 | 6/2020 |

OTHER PUBLICATIONS

De Luca et al. Metabolism, Clinical and Experimental, 2001, 50(7):739-741.*

Hatazawa et al. "PGC-1α-Mediated Branched-Chain Amino Acid Metabolism in the Skeletal Muscle" PLOS One, Mar. 2014, vol. 9, issue 3, 10 pages.

Chinese Office Action for Appl No. 202180079258.3 dated Oct. 21, 2025, 6 pages.

* cited by examiner

*Primary Examiner* — Rei Tsang Shiao
(74) *Attorney, Agent, or Firm* — K&L Gates LLP

(57) ABSTRACT

Compositions may be used for a variety of therapeutic applications, including treating and/or preventing a disease or disorder related to reduced or inadequate mitochondrial activity, in particular in condition of oxidative stress, such as aging, exercise, musculo-skeletal diseases, respiratory diseases, pain syndromes, neurodegenerative diseases and metabolic diseases. The compositions can contain a combination of a combination of at least one of glycine or a functional derivative thereof, and at least one large neutral amino acid and/or cationic amino acid or precursors thereof. The compositions can be food products or nutritional supplements.

20 Claims, 4 Drawing Sheets

COMPOSITIONS AND METHODS USING AT LEAST ONE GLYCINE OR DERIVATIVE THEREOF AND AT LEAST ONE LARGE NEUTRAL AMINO ACID AND/OR CATIONIC AMINO ACID OR PRECURSOR THEREOF

CROSS REFERENCE TO RELATED APPLICATIONS

The present application is a National Stage of International Application No. PCT/EP2021/084588, filed on Dec. 7, 2021, which claims priority to European Patent Application No. 20212799.9, filed on Dec. 9, 2020, the entire contents of which are being incorporated herein by reference.

TECHNICAL FIELD OF THE INVENTION

The present disclosure generally relates to compositions and methods that treat or prevent oxidative stress or a condition associated with oxidative stress, and/or a mitochondria-related disease or condition associated with altered mitochondrial function.

BACKGROUND OF THE INVENTION

Population aging has been a remarkable demographic event during the past decades. As the growth of the older population has outpaced the total population due to increased longevity, the proportion of older persons relative to the rest of the population has increased considerably. For example, one in every twelve individuals was at least 60 years of age in 1950, and one in every ten was aged 60 years or older by the end of 2000. By the end of 2050, the number of persons worldwide that is 60 years or over is projected to be one in every five.

Mitochondrial dysfunction, oxidative stress, altered intercellular communication (including chronic low-grade inflammation), genomic instability, telomere attrition, loss of proteostasis, altered nutrient sensing, epigenetic alterations, and stem cell exhaustion have been proposed as hallmarks of aging. Moreover, free radicals—reactive oxygen species (ROS)—are the main origin of aging by causing oxidative cellular injuries. Free radicals are necessary for many biochemical processes and they are produced as by-products during some biochemical reactions or as substrates for other biochemical reactions in each cell. As mitochondria are the principle source of intracellular reactive oxygen species (ROS), this hypothesis suggested a central role for the mitochondrion in normal mammalian aging. In recent years, however, much work has questioned the importance of mitochondrial ROS in driving aging. Conversely new evidence points to other facets of mitochondrial dysfunction which may nevertheless suggest the mitochondrion retains a critical role at the center of a complex web of processes leading to cellular and organismal aging.

Moreover, in humans, oxidative stress is involved in many diseases. Examples include atherosclerosis, Parkinson's disease, heart failure, myocardial infarction, Alzheimer's disease, schizophrenia, bipolar disorder, fragile X syndrome, and chronic fatigue syndrome.

Oxidative stress contributes to tissue injury following irradiation and hyperoxia. It is suspected to be important in neurodegenerative diseases, including Alzheimer's disease, Parkinson's disease, amyotrophic lateral sclerosis (ALS), and Huntington's disease. Oxidative stress is also thought to be linked to certain cardiovascular diseases, since oxidation of low-density lipoprotein (LDL) in the vascular endothelium is a precursor to plaque formation. Oxidative stress also plays a role in the ischemic cascade due to oxygen reperfusion injury following hypoxia. This cascade includes both strokes and heart attacks. Oxidative stress has also been implicated in chronic fatigue syndrome.

SUMMARY OF THE INVENTION

As detailed in the experimental data set forth later herein, the inventors found that the combination of compounds disclosed herein are able to support mitochondrial function in oxidative stress conditions, such as aging, exercise, musculo-skeletal diseases, respiratory diseases, pain syndromes, neurodegenerative diseases and metabolic diseases. In particular, by reducing oxidative stress and improving mitochondrial function, the present composition can treat, reduce incidence of, or reduce severity of metabolic and degenerative diseases at least with a combined effect, possibly potentiating each other or providing synergy.

Reduction of oxidative stress and improvement of mitochondrial function are mechanistically linked. Mitochondrial dysfunction contributes to cellular damage, partially through reactive oxygen species (ROS) and metabolic derangements, by not being able to metabolize nutrients, in turn leading to metabolic and degenerative diseases. Without being bound by theory, the present inventors have found that, in condition of oxidative stress, the demand of cationic and large neutral amino acids is increased. In particular, cationic amino acids transporter and large neutral amino acids transporters are overexpressed, thus suggesting a higher need of these amino acids to sustain mitochondrial function during high oxidative stress. Moreover, glycine is able to restore mitochondrial respiration after an acute oxidative stress.

Accordingly, in a general embodiment, the present disclosure provides a composition comprising an effective amount of a combination of at least one glycine or functional derivative thereof and at least one large neutral amino acid and/or cationic amino acid or precursors for use in treating or preventing i) a mitochondria-related disease or condition associated with altered mitochondrial function and/or ii) at least one physical state selected from the group consisting of oxidative stress or a condition associated with oxidative stress in an individual.

It is another object of the invention, to provide composition comprising an effective amount of a combination of at least one glycine or functional derivative thereof and at least one large neutral amino acid and/or cationic amino acid or precursors thereof, for use in delaying off-set of metabolic decline, maintaining muscle mass, decreasing oxidative stress, maintaining immune function and/or maintaining cognitive function in a healthy older adult.

It is a further object of the present invention to provide a composition comprising an effective amount of a combination of at least one glycine or functional derivative thereof and at least one large neutral amino acid and/or cationic amino acid or precursors thereof, for use in i) mitigating deleterious effects of aging, ii) improving at least one of muscle performance or muscle recovery from exercise, exercise capacity and/or physical function, iii) reducing severity of metabolic and/or degenerative diseases in an individual.

Another aspect of the present invention relates to a method of manufacturing a composition for use according to the invention.

An advantage of one or more embodiments provided by the present disclosure is to help off-set slowing of the metabolism associated with aging.

Yet another advantage of one or more embodiments provided by the present disclosure is to provide key amino acids as energy fuels to mitochondria thereby reducing the need to break down tissue protein, including muscle protein, to maintain adequate cellular energy production.

Yet another advantage of one or more embodiments provided by the present disclosure is to supplement key amino acids which become less available in cells in sufficient quantities in condition of oxidative stress.

Another advantage of one or more embodiments provided by the present disclosure is to help reduce oxidative stress on the body.

Additional features and advantages are described herein and will be apparent from the following Figures and Detailed Description.

DETAILED DESCRIPTION OF THE INVENTION

Definitions

Figure 1:
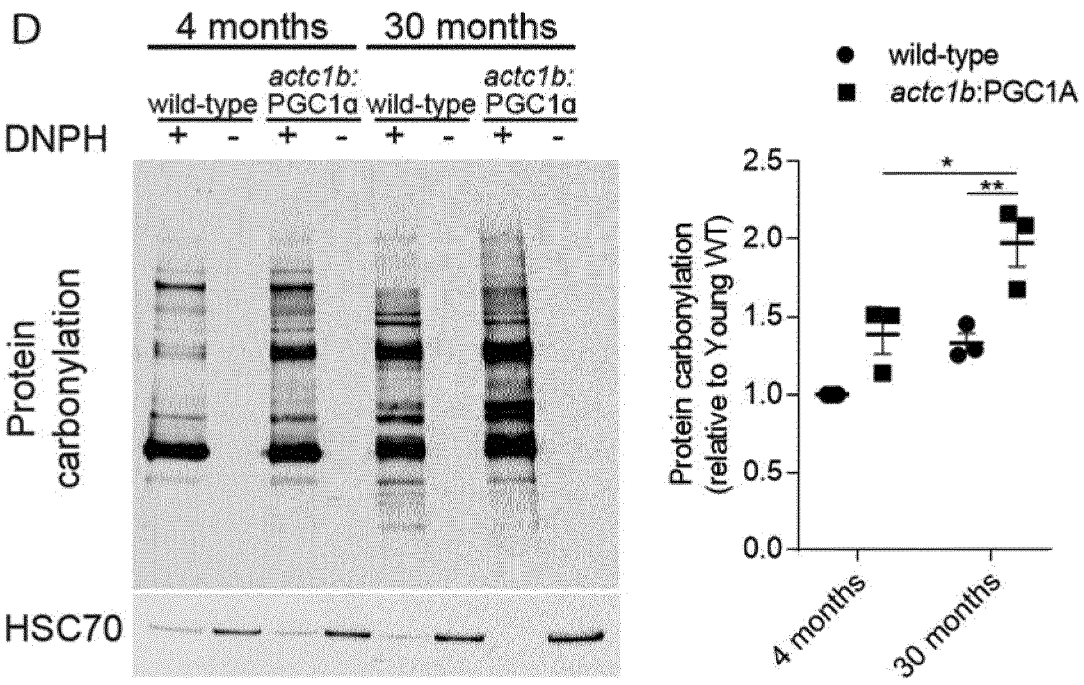
FIG. 1 is a graph showing increase of oxidative stress in PGC1A overexpressing fish during aging. Results are expressed as mean+/− SEM from n=3 experiments. Statistics have been done using 2-way Anova with a Tukey multiple comparison test. * p<0.05 ** p<0.01.

Some definitions are provided hereafter. Nevertheless, definitions may be located in the “Embodiments” section below, and the above header “Definitions” does not mean that such disclosures in the “Embodiments” section are not definitions.

All percentages expressed herein are by weight of the total weight of the composition unless expressed otherwise. As used herein, “about,” “approximately” and “substantially” are understood to refer to numbers in a range of numerals, for example the range of −10% to +10% of the referenced number, preferably −5% to +5% of the referenced number, more preferably −1% to +1% of the referenced number, most preferably −0.1% to +0.1% of the referenced number. All numerical ranges herein should be understood to include all integers, whole or fractions, within the range. Moreover, these numerical ranges should be construed as providing support for a claim directed to any number or subset of numbers in that range. For example, a disclosure of from 1 to 10 should be construed as supporting a range of from 1 to 8, from 3 to 7, from 1 to 9, from 3.6 to 4.6, from 3.5 to 9.9, and so forth.

As used in this disclosure and the appended claims, the singular forms “a,” “an” and “the” include plural referents unless the context clearly dictates otherwise. Thus, for example, reference to “a component” or “the component” includes two or more components.

The words “comprise,” “comprises” and “comprising” are to be interpreted inclusively rather than exclusively. Likewise, the terms “include,” “including” and “or” should all be construed to be inclusive, unless such a construction is clearly prohibited from the context. Nevertheless, the compositions disclosed herein may lack any element that is not specifically disclosed herein. Thus, a disclosure of an embodiment using the term “comprising” includes a disclosure of embodiments “consisting essentially of” and “consisting of” the components identified. A composition “consisting essentially of” contains at least 50 wt. % of the referenced components, preferably at least 75 wt. % of the referenced components, more preferably at least 85 wt. % of the referenced components, most preferably at least 95 wt. % of the referenced components.

The term “and/or” used in the context of “X and/or Y” should be interpreted as “X,” or “Y,” or “X and Y.” Similarly, “at least one of X or Y” should be interpreted as “X,” or “Y,” or “X and Y.” Where used herein, the terms “example” and “such as,” particularly when followed by a listing of terms, are merely exemplary and illustrative and should not be deemed to be exclusive or comprehensive. As used herein, a condition “associated with” or “linked with” another condition means the conditions occur concurrently, preferably means that the conditions are caused by the same underlying condition, and most preferably means that one of the identified conditions is caused by the other identified condition.

The terms “food,” “food product” and “food composition” mean a product or composition that is intended for ingestion by an individual such as a human and provides at least one nutrient to the individual. A food product typically includes at least one of a protein, a lipid, a carbohydrate and optionally includes one or more vitamins and minerals. The compositions of the present disclosure, including the many embodiments described herein, can comprise, consist of, or consist essentially of the elements disclosed herein, as well as any additional or optional ingredients, components, or elements described herein or otherwise useful in a diet. An “oral nutrition supplement” or “ONS” is a composition comprising at least one macronutrient and/or at least one micronutrient, for example in a form of sterile liquids, semi-solids or powders, and intended to supplement other nutritional intake such as that from food. Non-limiting examples of commercially available ONS products include MERITENE®, BOOST®, NUTREN® and SUSTAGEN®. In some embodiments, an ONS can be a beverage in liquid form that can be consumed without further addition of liquid, for example an amount of the liquid that is one serving of the composition.

As used herein, the term “isolated” means removed from one or more other compounds or components with which the compound may otherwise be found, for example as found in nature. For example, “isolated” preferably means that the identified compound is separated from at least a portion of the cellular material with which it is typically found in nature. In an embodiment, an isolated compound is pure, i.e., free from any other compound.

“Prevention” includes reduction of risk and/or severity of a condition or disorder. The terms “treatment,” “treat” and “to alleviate” include both prophylactic or preventive treatment (that prevent and/or slow the development of a targeted pathologic condition or disorder) and curative, therapeutic or disease-modifying treatment, including therapeutic measures that cure, slow down, lessen symptoms of, and/or halt progression of a diagnosed pathologic condition or disorder; and treatment of patients at risk of contracting a disease or suspected to have contracted a disease, as well as patients who are ill or have been diagnosed as suffering from a disease or medical condition. The term does not necessarily imply that a subject is treated until total recovery. The terms “treatment” and “treat” also refer to the maintenance and/or promotion of health in an individual not suffering from a disease but who may be susceptible to the development of an unhealthy condition. The terms “treatment,” “treat” and “to alleviate” are also intended to include the potentiation or otherwise enhancement of one or more primary prophylactic or therapeutic measure. The terms “treatment,” “treat” and “to alleviate” are further intended to include the dietary management of a disease or condition or the dietary management for prophylaxis or prevention a disease or condition. A treatment can be patient- or doctor-related.

A “subject” or “individual” is a mammal, preferably a human. The term “elderly” in the context of a human means an age from birth of at least 60 years, preferably above 63 years, more preferably above 65 years, and most preferably above 70 years. The term “older adult” in the context of a human means an age from birth of at least 45 years, preferably above 50 years, more preferably above 55 years, and includes elderly individuals. As used herein, an “effective amount” is an amount that prevents a deficiency, treats a disease or medical condition in an individual, or, more generally, reduces symptoms, manages progression of the disease, or provides a nutritional, physiological, or medical benefit to the individual.

“Animal” includes, but is not limited to, mammals, which includes but is not limited to rodents; aquatic mammals; domestic animals such as dogs, cats and other pets; farm animals such as sheep, pigs, cows and horses; and humans. Where “animal,” “mammal” or a plural thereof is used, these terms also apply to any animal that is capable of the effect exhibited or intended to be exhibited by the context of the passage, e.g., an animal benefitting from improved mitochondrial calcium import. While the term “individual” or “subject” is often used herein to refer to a human, the present disclosure is not so limited. Accordingly, the term “individual” or “subject” refers to any animal, mammal or human that can benefit from the methods and compositions disclosed herein.

As used herein, “neurodegenerative disease” or “neurodegenerative disorder” refers to any condition involving progressive loss of functional neurons in the central nervous system. In an embodiment, the neurodegenerative disease is associated with age-related cell death. Non-limiting examples of neurodegenerative diseases include Alzheimer's disease, Parkinson's disease, Huntington's disease, amyotrophic lateral sclerosis (also known as ALS and as Lou Gehrig's disease), AIDS dementia complex, adrenoleukodystrophy, Alexander disease, Alper's disease, ataxia telangiectasia, Batten disease, bovine spongiform encephalopathy (BSE), Canavan disease, corticobasal degeneration, Creutzfeldt-Jakob disease, dementia with Lewy bodies, fatal familial insomnia, frontotemporal lobar degeneration, Kennedy's disease, Krabbe disease, Lyme disease, Machado-Joseph disease, multiple sclerosis, multiple system atrophy, neuroacanthocytosis, Niemann-Pick disease, Pick's disease, primary lateral sclerosis, progressive supranuclear palsy, Refsum disease, Sandhoff disease, diffuse myelinoclastic sclerosis, spinocerebellar ataxia, subacute combined degeneration of spinal cord, tabes dorsalis, Tay-Sachs disease, toxic encephalopathy, transmissible spongiform encephalopathy, and wobbly hedgehog syndrome.

As used herein “cognitive performance” refers to how well a subject performs one or more cognitive function. As used herein, “cognitive function” refers to any mental process by which one becomes aware of, perceives, or comprehends ideas. It involves all aspects of perception, thinking, reasoning, and remembering and includes, for example, perception, memory, attention, speech comprehension, speech generation, reading comprehension, creation of imagery, learning, and reasoning. Ordinarily it will refer to at least memory.

Methods for measuring cognitive function are well-known and can include, for example, individual or battery tests for any aspect of cognitive function. One such test is the Prudhoe Cognitive Function Test by Margallo-Lana et al. (2003) J. Intellect. Disability Res. 47:488-492. Another such test is the Mini Mental State Exam (MMSE), which is designed to assess orientation to time and place, registration, attention and calculation, recall, language use and comprehension, repetition, and complex commands. Folstein et al. (1975) J. Psych. Res. 12:189-198. Other tests useful for measuring cognitive function include the Alzheimer Disease Assessment Scale-Cognitive (ADAS-Cog) and the Cambridge Neuropsychological Test Automated Battery (CANTAB). Such tests can be used to assess cognitive function in an objective manner, so that changes in cognitive function, for example in response to treatment in accordance with methods disclosed herein, can be measured and compared.

As used herein, a “cognitive disorder” refers to any condition that impairs cognitive function. Non-limiting examples of a cognitive disorder include delirium, dementia, learning disorder, attention deficit disorder (ADD), and attention deficit hyperactivity disorder (ADHD). A “stress-induced or stress-related cognitive dysfunction” refers to a disturbance in cognitive function that is induced or related to stress.

All references to singular characteristics or limitations of the present invention shall include the corresponding plural characteristic or limitation, and vice versa, unless otherwise specified or clearly implied to the contrary by the context in which the reference is made.

Unless defined otherwise, all technical and scientific terms used herein have the same meaning as commonly understood by one of ordinary skill in the art.

Embodiments

The present disclosure provides compositions comprising an effective amount of a combination of at least one glycine or functional derivative thereof and at least one large neutral amino acid and/or cationic amino acid or precursors.

In an embodiment, at least one glycine or functional derivative thereof is selected from the group consisting of L-glycine, L-glycine ethyl ester, D-Allylglycine; N-[Bis (methylthio)methylene]glycine methyl ester; Boc-allyl-Gly-OH (dicyclohexylammonium) salt; Boc-D-Chg-OH; Boc-Chg-OH; (R)-N-Boc-(2'-chlorophenyl)glycine; Boc-L-cyclopropylglycine; Boc-L-cyclopropylglyci ne; (R)-N-Boc-4-fluorophenylglycine; Boc-D-propargylglycine; Boc-(S)-3-thienylglycine; Boc-(R)-3-thienylglycine; D-a-Cyclohexylglycine; L-a-Cyclopropylglycine; N-(2-fluorophenyl)-N-(methylsulfonyl)glycine; N-(4-fluorophenyl)-N-(methylsulfonyl)glycine; Fmoc-N-(2,4-dimethoxybenzyl)-Gly-OH; N-(2-Furoyl)glycine; L-a-Neopentylglycine; D-Propargylglycine; sarcosine; Z-a-Phosphonoglycine trimethyl ester, and mixtures thereof.

Non limiting examples of suitable large neutral amino acids include Leucine, Isoleucine, Valine, Phenylalanine, Tyrosine, Tryptophan, Threonine, Methionine and Histidine and mixtures thereof. Non-limiting examples of suitable cationic amino acid include Arginine, Lysine or Ornithine. Precursors of said amino acids may be advantageously used in the present composition and are known in the art (see KEGG PATHWAY (www.genome.jp/kegg/pathway.html).

The composition can comprise one or more of Leucine, Isoleucine, Valine, Phenylalanine, Tyrosine, Tryptophan, Threonine, Methionine and Histidine, in free form and/or bound as peptides and/or proteins such as dairy, animal or plant proteins. Whey protein is rich in BCAAs such as Leucine and Isoleucine. Therefore, some embodiments of the composition comprise whey protein that provides at least a portion of the large neutral amino acids in the composition.

In another embodiment, known metabolite of the amino acids may be used, for example 2-Hydroxyisocaproic acid (HICA) as a metabolite of leucine may advantageously be used.

In another embodiment, collagen and collagen peptides may be used as source of glycine. Some plant-based protein source may also provide source of glycine.

A daily dose of the composition can include one or more of 0.1-100 mg/kg body weight (bw) Glycine, 0.175-142.85 mg/kg bw Leucine, preferably 0.35-71.425 mg/kg bw Leucine; 0.175-71.425 mg/kg bw Isoleucine; 5-340 mg/kg bw Valine; 20-153 mg/kg bw Phenylalanine; 20-126 mg/kg bw Tyrosine; 2.86-42.86 mg/kg bw Tryptophan; 7-85 mg/kg bw Threonine; 3-43 mg/kg bw Methionine; 12.86-80 mg/kg bw Histidine; 20-300 mg/kg bw Arginine, preferably 50-200 mg/kg bw Arginine; 20-300 mg/kg bw Ornithine, preferably 100-200 mg/kg bw Ornithine; 12-72 mg/kg bw Lysine. The daily dose of the one or more large neutral amino acids or cationic amino acid can be provided by one or more servings of the composition per day. When several large neutral amino acids and/or cationic amino acids are combined in the composition, the minimal amount of each amino acid as described above may be reduced accordingly; also the maximal amount of each amino acid in said composition may not exceed the values described above.

In an embodiment, the at least one glycine or functional derivative thereof and the at least one large neutral amino acid and/or cationic amino acid or precursors are administered in the same composition.

In an embodiment, the at least one glycine or functional derivative thereof and at least one large neutral amino acid and/or cationic amino acid or precursors are administered in a different composition relative to the remainder of the combination.

Each of the compounds can be administered at the same time as the other compounds (i.e., as a single unit) or separated by a time interval (i.e., in separate units).

Ingredients-Further Bioactive Compound

The compositions for use according to the invention may also comprise at least one further bioactive compound selected from the group consisting of antioxidants, anti-inflammatory compounds, glycosaminoglycans, prebiotics, fibers, probiotics, fatty acids, enzymes, minerals, trace elements and/or vitamins.

The term "bioactive" in the context of the present application means that the compound contributes to the health of an individual, or has an effect on the human body, beyond that of meeting basic nutritional need. The at least one further bioactive compound may be from a natural source. Thus the compounds may be from extracts of plants, animals, fish, fungi, algae, microbial fermentation. Minerals are considered as from natural source also within this definition.

Nutritional Compositions

The compositions for use according to the invention may be nutritional compositions or pharmaceutical compositions, and may be for human or veterinary use. In an embodiment, the combination is administered orally.

Thus, in preferred embodiments, the composition for use according to the invention is a nutritional composition.

By "nutritional composition" is meant in the context of the present application a composition which is a source of nutrition to an individual.

The nutritional products or compositions of the invention may be a source of complete nutrition or may be a source of incomplete nutrition. As used herein, "complete nutrition" includes nutritional products and compositions that contain sufficient types and levels of macronutrients (protein, fats and carbohydrates) and micronutrients to be sufficient to be a sole source of nutrition for the animal to which it is being administered to. Patients can receive 100% of their nutritional requirements from such complete nutritional compositions. As used herein, "incomplete nutrition" includes nutritional products or compositions that do not contain sufficient levels of macronutrients (protein, fats and carbohydrates) or micronutrients to be sufficient to be a sole source of nutrition for the animal to which it is being administered to. Partial or incomplete nutritional compositions can be used as a nutritional supplement.

Non-limiting examples of suitable compositions for the include food compositions, dietary supplements, dietary supplements (e.g., liquid ONS), complete nutritional compositions, beverages, pharmaceuticals, oral nutritional supplement, medical food, nutraceuticals, food for special medical purpose (FSMP), powdered nutritional products to be reconstituted in water or milk before consumption, food additives, medicaments, drinks, petfood, and combinations thereof.

In an embodiment, the compositions for use according to the invention include a source of protein. The protein source may be dietary protein including, but not limited to animal protein (such as milk protein, meat protein or egg protein), vegetable protein (such as soy protein, wheat protein, rice protein, and pea protein), or combinations thereof. In an embodiment, the protein is selected from the group consisting of whey, chicken, corn, caseinate, wheat, flax, soy, carob, pea or combinations thereof.

In an embodiment, the compositions include a source of carbohydrates. Any suitable carbohydrate may be used in the present compositions including, but not limited to, starch, sucrose, lactose, glucose, fructose, corn syrup solids, maltodextrin, modified starch, amylose starch, tapioca starch, corn starch, xylitol, sorbitol or combinations thereof.

In an embodiment, the compositions include a source of fat. The source of fat may include any suitable fat or fat mixture. For example, the fat source may include, but is not limited to, vegetable fat (such as olive oil, corn oil, sunflower oil, high-oleic sunflower, rapeseed oil, canola oil, hazelnut oil, soy oil, palm oil, coconut oil, blackcurrant seed oil, borage oil, lecithins, and the like), animal fats (such as milk fat), or combinations thereof. The source of fat may also be less refined versions of the fats listed above (e.g., olive oil for polyphenol content).

In addition, compositions for use according to the invention may also comprise natural or artificial flavours, for example fruit flavours like banana, orange, peach, pineapple or raspberry or other plant flavours like vanilla, cocoa, coffee, etc.

Nutritional Composition Formats

The nutritional compositions may include, besides the main bioactive components and any further bioactive components, and optionally one or more of a protein, carbohydrate and fat source, any number of optional additional food ingredients, including conventional food additives (synthetic or natural), for example one or more acidulants, additional thickeners, buffers or agents for pH adjustment, chelating agents, colorants, emulsifiers, excipient, flavor agent, mineral, osmotic agents, a pharmaceutically acceptable carrier, preservatives, stabilizers, sugar, sweeteners, texturizers, and/or vitamins. The optional ingredients can be added in any suitable amount.

The nutritional composition may be provided in any suitable format. Examples of nutritional composition formats in which the composition for use according to the invention may be provided include solutions, ready-for-consumption compositions (e.g. ready-to-drink compositions or instant drinks), liquid comestibles, soft drinks, juice, sports drinks, milk drinks, milk-shakes, yogurt drinks, soup, etc.

In another embodiment, the nutritional compositions may be provided in the form of a concentrate, a powder, or granules (e.g. effervescent granules), which are diluted with water or other liquid, such as milk or fruit juice, to yield the ready-for-consumption composition.

Further nutritional composition formats include, baked products, dairy products, desserts, confectionery products, cereal bars, and breakfast cereals. Examples of dairy products include milk and milk drinks, yoghurts and other cultured milk products, ice creams and cheeses. Examples of baked products include bread, biscuits and cakes.

In one embodiment, the composition for use according to the invention may also be available in a great variety of formats designed as animal foods, in particular for the dog or the cat, whether in a wet form, semi-wet form or dry form, in particular in the form of biscuits.

The compositions disclosed herein can use any of a variety of formulations for therapeutic administration. More particularly, pharmaceutical compositions can comprise appropriate pharmaceutically acceptable carriers or diluents and may be formulated into preparations in solid, semi-solid, liquid or gaseous forms, such as tablets, capsules, powders, granules, ointments, solutions, suppositories, injections, inhalants, gels, microspheres, and aerosols. As such, administration of the composition can be achieved in various ways, including oral, buccal, rectal, parenteral, intraperitoneal, intradermal, transdermal, and intratracheal administration. The active agent may be systemic after administration or may be localized by the use of regional administration, intramural administration, or use of an implant that acts to retain the active dose at the site of implantation.

In pharmaceutical dosage forms, the compounds may be administered as their pharmaceutically acceptable salts. They may also be used in appropriate association with other pharmaceutically active compounds. The following methods and excipients are merely exemplary and are in no way limiting.

For oral preparations, the compounds can be used alone or in combination with appropriate additives to make tablets, powders, granules or capsules, for example, with conventional additives, such as lactose, mannitol, corn starch or potato starch; with binders, such as crystalline cellulose, cellulose functional derivatives, acacia, corn starch or gelatins; with disintegrators, such as corn starch, potato starch or sodium carboxymethylcellulose; with lubricants, such as talc or magnesium stearate; and if desired, with diluents, buffering agents, moistening agents, preservatives and flavoring agents.

Routes of Administration

The nutritional compositions of the present disclosure may be administered by any means suitable for human administration, and in particular for administration in any part of the gastrointestinal tract. Enteral administration, oral administration, and administration through a tube or catheter are all covered by the present disclosure. The nutritional compositions may also be administered by means selected from oral, rectal, sublingual, sublabial, buccal, topical, etc.

The nutritional compositions may be administered in any known form including, for example, tablets, capsules, liquids, chewables, soft gels, sachets, powders, syrups, liquid suspensions, emulsions and solutions in convenient dosage forms. In soft capsules, the active ingredients are preferably dissolved or suspended in suitable liquids, such as fatty oils, paraffin oil or liquid polyethylene glycols. Optionally, stabilizers may be added.

If the nutritional compositions are administered by tube feeding, the nutritional compositions may be used for short term or long term tube feeding.

The composition can be administered to an individual such as a human, e.g., an ageing individual or a critically ill individual, in a therapeutically effective dose. The therapeutically effective dose can be determined by the person skilled in the art and will depend on a number of factors known to those of skill in the art, such as the severity of the condition and the weight and general state of the individual.

The composition is preferably administered to the individual at least one day per week, preferably at least two days per week, more preferably at least three days per week, most preferably all seven days of the week; for at least one week, at least one month, at least two months, at least three months, at least six months, or even longer. In some embodiments, the composition is administered to the individual consecutively for a number of days, for example at least until a therapeutic effect is achieved. In an embodiment, the composition can be administered to the individual daily for at least 30, 60 or 90 consecutive days.

In some embodiments, the administration continues for the remaining life of the individual. In other embodiments, the administration occurs until no detectable symptoms of the medical condition remain. In specific embodiments, the administration occurs until a detectable improvement of at least one symptom occurs and, in further cases, continues to remain ameliorated.

The above examples of administration do not require continuous daily administration with no interruptions. Instead, there may be some short breaks in the administration, such as a break of two to four days during the period of administration. The ideal duration of the administration of the composition can be determined by those of skill in the art.

Method of Treatment

Mitochondrial diseases are the result of either inherited or spontaneous mutations in mitochondrial DNA or nuclear DNA which lead to altered functions of the proteins or RNA molecules that normally reside in mitochondria. Problems with mitochondrial function, however, may only affect certain tissues as a result of factors occurring during development and growth that are not yet fully understood. Even when tissue-specific isoforms of mitochondrial proteins are considered, it is difficult to explain the variable patterns of affected organ systems in the mitochondrial disease syndromes seen clinically.

Mitochondrial diseases result from failures of the mitochondria, specialized compartments present in every cell of the body except red blood cells. Mitochondria are responsible for creating more than 90% of the energy needed by the body to sustain life and support growth. When they fail, less and less energy is generated within the cell. Cell injury and even cell death follow. If this process is repeated throughout the body, whole systems begin to fail, and the life of the person in whom this is happening is severely compromised. Mitochondrial diseases primarily affect children, but adult onset is becoming more recognized. Diseases of the mitochondria appear to cause the most damage to cells of the brain, heart, liver, skeletal muscles, kidney, and the endocrine and respiratory systems.

Many symptoms in mitochondrial disorders are nonspecific. The symptoms may also show an episodic course, with periodic exacerbations. The episodic condition of migraine, as well as myalgia, gastrointestinal symptoms, tinnitus, depression, chronic fatigue, and diabetes, have been mentioned among the various manifestations of mitochondrial disorders in review papers on mitochondrial medicine (Chinnery and Turnbull (1997) QJM 90:657-67; Finsterer (2004) Eur. J. Neurol. 11:163-86). In patients with mitochondrial disorders, clinical symptomatology typically occurs at times of higher energy demand associated with physiological stressors, such as illness, fasting, over-exercise, and environmental temperature extremes. Furthermore, psychological stressors also frequently trigger symptomatology, presumably due to higher brain energy demands for which the patient is unable to match with sufficient ATP production.

Depending on which cells are affected, symptoms may include loss of motor control, muscle weakness and pain, gastro-intestinal disorders and swallowing difficulties, poor growth, cardiac disease, liver disease, diabetes, respiratory complications, seizures, visual/hearing problems, lactic acidosis, developmental delays and susceptibility to infection. Mitochondrial diseases include, without limitation, Alper's disease; Barth syndrome; beta-oxidation defects; carnitine deficiency; carnitine-acyl-carnitine deficiency; chronic progressive external ophthalmoplegia syndrome; co-enzyme Q10 deficiency; Complex I deficiency; Complex II deficiency; Complex III deficiency; Complex IV deficiency; Complex V deficiency; CPT I deficiency; CPT II deficiency; creatine deficiency syndrome; cytochrome c oxidase deficiency; glutaric aciduria type II; Kearns-Sayre syndrome; lactic acidosis; LCHAD (long-chain acyl-CoA dehydrogenase deficiency); Leber's hereditary optic neuropathy; Leigh disease; lethal infantile cardiomyopathy; Luft disease; MAD (medium-chain acyl-CoA dehydrogenase deficiency); mitochondrial cytopathy; mitochondrial DNA depletion; mitochondrial encephalomyopathy, lactic acidosis, and stroke-like symptoms; mitochondrial encephalopathy; mitochondrial myopathy; mitochondrial recessive ataxia syndrome; muscular dystrophies, myoclonic epilepsy and ragged-red fiber disease; myoneurogenic gastrointestinal encephalopathy; neuropathy, ataxia, retinitis pigmentosa, and ptosis; Pearson syndrome; POLG mutations; pyruvate carboxylase deficiency; pyruvate dehydrogenase deficiency; SCHAD (short-chain acyl-CoA dehydrogenase deficiency); and very long-chain acyl-CoA dehydrogenase deficiency.

Accordingly, an aspect of the present disclosure is a composition comprising an effective amount of a combination of at least one glycine or functional derivative thereof and at least one large neutral amino acid and/or cationic amino acid or precursors thereof, for use to treat and/or prevent i) a mitochondria-related disease or condition associated with altered mitochondrial function and/or ii) at least one physical state selected from the group consisting of oxidative stress or a condition associated with oxidative stress in an individual.

In an embodiment, the amount of the combination can be effective to treat or prevent a mitochondria-related disease or condition selected from the group consisting of stress, obesity, reduced metabolic rate, metabolic syndrome, diabetes mellitus, complications from diabetes, cardiovascular disease, respiratory diseases, pain syndromes, hyperlipidemia, neurodegenerative disease, cognitive disorder, stress-induced or stress-related cognitive dysfunction, mood disorder, anxiety disorder, age-related neuronal death or dysfunction, musculo-skeletal disorder, sarcopenia, frailty, pre-frailty, chronic kidney disease, macular degeneration, and combinations thereof.

In an embodiment, the at least one physical state is selected from the group consisting of deleterious effects of aging, muscle loss, pre-diabetes, gestational diabetes, type I diabetes, type II diabetes, complications from diabetes, insulin resistance, metabolic syndrome, dyslipidemia, overweight, obesity, raised cholesterol levels, raised triglyceride levels, elevated fatty acid levels, fatty liver disease, renal disease, cardiovascular disease, musculo-skeletal diseases, respiratory diseases, pain syndromes, neurodegenerative disease, impaired cognitive function, myopathy such as statin-induced myopathy, non-alcoholic steatohepatitis, tinnitus, dizziness, alcohol hangover, hearing impairment, osteoporosis, hypertension, atherosclerosis/coronary artery disease, myocardial damage after stress, traumatic brain injury, cystic fibrosis, inflammation, cancer, and HIV infection.

In another embodiment, the present disclosure provides a method of delaying NAFLD, delaying HIV, fighting the effects of ageing from within, off-setting metabolic decline, maintaining muscle mass, decreasing oxidative stress, maintaining immune function and/or maintaining cognitive function in a healthy older adult. The healthy older adult can be elderly.

In another embodiment, the present disclosure provides a method of enhancing the metabolization of reactive oxygen species, improving glucose control and/or improving muscle function in an individual with at least one of obesity, pre-diabetes or diabetes.

In another embodiment, the present disclosure provides a method of improving or maintaining cognitive function. The cognitive function can be selected from the group consisting of perception, memory, attention, speech comprehension, speech generation, reading comprehension, creation of imagery, learning, reasoning, and combinations thereof. In an embodiment, the individual does not have a cognitive disorder. The individual can be elderly.

In another embodiment, the present disclosure provides a method of enhancing at least one of cognitive performance or muscle performance. The combination can enhance cognitive performance comprising memory. The combination can enhance muscle performance comprising at least one of strength, speed or endurance. The individual can be elderly.

In another embodiment, the present disclosure provides a method of achieving at least one result selected from the group consisting of (i) reducing severity and/or incidence of effects of aging, (ii) maintaining or improving cellular functioning and/or overall health, (iii) supporting at least one of normal mitochondrial function, cellular protection, or energy metabolism, (iv) increasing daily energy level, (v) reducing fatigue, (vi) maintaining or improving physical energy (vii) promoting healthy aging by promoting healthy or normal cellular function, (viii) supporting healthy skin, (ix) treating heart failure and/or reducing severity or incidence of heart failure, (x) treating, reducing incidence of, or reducing severity of oxidative stress and/or reduced glutathione (GSH) experienced during a time period comprising a stay in an intensive care unit (ICU), (xi) treating, reducing incidence of, or reducing severity of another condition associated with oxidative stress and/or reduced GSH, (xii) promoting rehabilitation from injury, illness or surgery, (postoperative, post stroke, post fractures/joint replacement etc) for improvement of functional performance (exercise tolerance, muscle contraction, fatigue) (xiii) modulating NAD+ levels in a patient having cancer or in remission from cancer, (xiv) treating, reducing incidence of, or reducing severity of symptoms from bariatric surgery, (xv) treating, reducing incidence of, or reducing severity of non-alcoholic fatty liver disease (NAFLD), (xvi) treating, reducing incidence of, or reducing severity of human immunodeficiency virus infection (HIV), and (xvii) combinations thereof.

Another aspect of the present disclosure is a method of preventing at least one of these conditions, the method comprising administering to an individual at risk of the at least one condition a composition comprising a prophylactically effective amount of a combination of at least one glycine or functional derivative thereof, and at least one large neutral amino acid and/or cationic amino acid or precursors thereof.

In an embodiment of these methods, the hyperlipidemia that is treated or prevented comprises hypertriglyceridemia. In an embodiment of these methods, the hyperlipidemia that is treated or prevented comprises elevated free fatty acids. In an embodiment of these methods, the age-related neuronal death or dysfunction that is treated or prevented is by administration of the composition to an older adult, such as an elderly individual, e.g., an elderly individual with sarcopenia.

Another aspect of the present disclosure is a method of delaying off-set of metabolic decline, maintaining muscle mass, decreasing oxidative stress, maintaining immune function and/or maintaining cognitive function in a healthy older adult.

In an embodiment, the metabolic decline is fatty liver oxidative damage.

Another aspect of the present disclosure is a method of improving mitochondrial function in an individual with sarcopenia. The method comprises administering to the individual an effective amount of a combination of at least one glycine or functional derivative thereof, and at least one large neutral amino acid and/or cationic amino acid or precursors thereof.

Yet another aspect of the present disclosure is a method of enhancing metabolizing of reactive oxygen species, improving glucose control and/or improving muscle function in an individual with at least one of obesity, pre-diabetes or diabetes.

Another aspect of the present disclosure is a composition comprising a combination of at least one glycine or functional derivative thereof, and at least one large neutral amino acid and/or cationic amino acid or precursors thereof, in a total amount effective to increase at least one of muscle performance or cognitive performance (e.g., memory). In a related embodiment, a method of increasing at least one of muscle performance or cognitive performance (e.g., memory) in an individual comprises administering to the individual a composition comprising an effective amount of a combination of at least one glycine or functional derivative thereof, and at least one large neutral amino acid and/or cationic amino acid or precursors thereof.

Further regarding muscle performance, the increased muscle performance may be one or more of improved muscle function, reduced decline in muscle function, improved muscle strength, improved muscle endurance and improved muscle recovery. The composition can improve physical endurance (e.g., ability to perform a physical task such as exercise, physical labor, sports activities), inhibit or retard physical fatigue, enhance blood oxygen levels, enhance energy in healthy individuals, enhance working capacity and endurance, reduce muscle fatigue, reduce stress, enhance cardiac and cardiovascular function, improve sexual ability, increase muscle ATP levels, and/or reduce lactic acid in blood. “Endurance capacity” refers to the time to fatigue when exercising at a constant workload, generally at an intensity <80% V02max. In some embodiments, the composition is administered in an amount that increases mitochondrial activity, increases mitochondrial biogenesis, and/or increases mitochondrial mass.

In some embodiments, the composition is administered to an individual having impaired physical performance, impaired endurance capacity, and/or impaired muscle function. Improved muscle function can be particularly beneficial in elderly subjects with reduced muscle function as a result of an age-related condition. For example, a subject who may benefit from improved muscle function may experience a decline in muscle function which then leads to pre-frailty and frailty. Such subjects may not necessarily experience muscle wastage in addition to their decline in muscle function. Some subjects do experience both muscle wasting and a decline in muscle function, for example subjects with sarcopenia. The composition may enhance muscle performance in a subject who is frail or pre-frail.

Sports performance refers to the ability of an athlete’s muscles to perform when participating in sports activities. Enhanced sports performance, strength, speed, and endurance are measured by an increase in muscular contraction strength, an increase in amplitude of muscle contraction, or a shortening of muscle reaction time between stimulation and contraction. “Athlete” refers to an individual who participates in sports at any level and who seeks to achieve an improved level of strength, speed, or endurance in their performance, such as, for example, body builders, bicyclists, long distance runners, and short distance runners. Enhanced sports performance is manifested by the ability to overcome muscle fatigue, ability to maintain activity for longer periods of time, and have a more effective workout.

The compositions and the methods disclosed herein can also be effective in the treatment of muscle-related pathological conditions, including myopathies; neuromuscular diseases, such as Duchenne muscular dystrophy; acute sarcopenia, for example, muscle atrophy; and/or cachexia associated with burns, bed rest, limb immobilization, or major thoracic, abdominal, and/or orthopedic surgery.

The composition can treat or prevent sarcopenia, sarcopenic obesity, or cachexia, for example cachexia from an underlying medical condition such as chronic illness, HIV, cancer, chronic obstructive pulmonary disease (COPD), and/or aging in otherwise healthy individuals. In this regard, aging can be accompanied by reduction of NAD+ and glutathione (GSH). The composition can treat or prevent an eye condition resulting directly or indirectly from low GSH levels, including low levels in the lens of the eye that is known for being rich in glutathione. Non-limiting examples of such conditions include cataracts and/or glaucoma, presbyopia (loss of near vision with aging requiring reading glasses), and presbyacusis (loss of hearing with aging, which requires a hearing aid).

In an embodiment, the composition improves at least one of muscle performance or muscle recovery, such as from muscle stress, including muscle stress associated with exercise. The exercise may be of any kind, including aerobic ("cardio") exercise and/or weight training, for example. The composition can be administered during at least one time selected from the group consisting of before the exercise (e.g., less than one hour before), during the exercise, and after the exercise (e.g., less than one hour after the exercise).

A further aspect of the present disclosure is a composition comprising a combination of at least one glycine or functional derivative thereof, and at least one large neutral amino acid and/or cationic amino acid or precursors thereof in an amount effective to increase or maintain at least one of mitochondrial function or metabolic rate. In a related embodiment, a method of increasing or maintaining at least one of mitochondrial function or metabolic rate in an individual comprises administering to the individual a composition comprising an effective amount of a combination of at least one glycine or functional derivative thereof, and at least one large neutral amino acid and/or cationic amino acid or precursors thereof.

Another aspect of the present disclosure is a composition comprising a combination of at least one glycine or functional derivative thereof, and at least one large neutral amino acid and/or cationic amino acid or precursors thereof, in a total amount effective to improve or maintain cognitive function. In a related embodiment, a method of improving or maintaining cognitive function in an individual comprises administering to the individual the composition comprising a prophylactically effective amount of a combination of at least one glycine or functional derivative thereof, and at least one large neutral amino acid and/or cationic amino acid or precursors thereof.

In an embodiment, the individual does not have a cognitive disorder. For example, the composition can enhance cognitive function in a subject having normal cognitive function.

The compositions disclosed herein can also be used in the treatment of any of a variety of additional diseases and conditions in which defective or diminished mitochondrial activity participates in the pathophysiology of the disease or condition, or in which increased mitochondrial function will yield a desired beneficial effect.

Method of Manufacturing a Nutritional Composition of the Invention

The invention relates in a further aspect to a method for manufacturing a nutritional composition for use according to the invention, said method comprising the step of:

providing ingredients for a nutritional composition comprising a combination of oleuropein and/or metabolite thereof and quercetin and/or derivative thereof, and mixing, such that the nutritional composition comprises the combination of oleuropein and/or metabolite thereof and quercetin and/or derivative thereof.

Combination of Disclosures

It should be noted that embodiments and features described in the context of one of the aspects of the present invention also apply to the other aspects of the invention.

The compositions for use according to the invention are herein described in different parameters, such as the ingredients, nutritional composition formats, uses, target groups etc. It should be noted that embodiments and features described in the context of one of the parameters of the composition for use according to the invention, may also be combined with other embodiments and features described in the context of another parameter, unless expressly stated otherwise.

All patent and non-patent references cited in the present application, are hereby incorporated by reference in their entirety.

The invention will now be described in further details in the following non-limiting examples.

Examples

The following non-limiting examples present experimental data supporting the compositions and methods disclosed herein.

Materials and Methods

Zebrafish Husbandry and Transgenic Lines Generation

Adult AB zebrafish were raised at 28° C. under standard husbandry conditions. All experimental procedures were carried out according to the Swiss and EU ethical guidelines and were approved by the animal experimentation ethical committee of Canton of Vaud (permit VD3177). Transgenic zebrafish were generated using I-SCEI meganuclease mediated insertion into one-cell stage AB embryos of a construct harboring the zebrafish ppargc1a or the human PPARGC1A cDNA fused to a triple Flag sequence under the control of the skeletal muscle-specific actc1b promoter. For rapid selection of transgenic animals, the injected constructs carried an eye-marker cassette harboring ZsGreen under the control of the cryaa (alpha-crystallin A chain) promoter in reverse direction. Transgenic carriers were outcrossed with AB fish to raise transgenic and wild-type siblings.

Oxyblots

Carbonylated proteins in frozen skeletal muscle were measured using the Oxidized Protein Detection Kit (Abcam, #ab178020) according to the manufacturer's instructions. Quantification of the oxidized proteins was done processing and analyzing oxyblots with ImageJ (1.51 h, NIH).

RNA-Seq and Analysis

For gene expression analysis, flash frozen skeletal muscle was lysed in Qiazol with the FastPrep®-24 tissue homogenizer (MP-Biomedials). Total mRNA was extracted using the QlAcube plateform and mRNAeasy kit (Qiagen). RNA quantification was performed with Ribogreen (Life Technologies) and quality was assessed on a Fragment Analyzer (Advances Analytical). Sequencing libraries were prepared from 250 ng RNA using the TruSeq Stranded mRNA LT Sample Prep Kit (Illumina) following the manufacturer's protocol, except for the PCR amplification step. The latter was run for 15 cycles with the KAPA HiFi HotStart ReadyMix (Kapa BioSystems). This optimal PCR cycle number has been evaluated using the Cycler Correction Factor method as previously described (Atger et al., Proc Natl Acad Sci USA. 2015 Nov. 24; 112(47):E6579-88). Libraries were quantified with Picogreen (Life Technologies). The size pattern was controlled with the DNA High Sensitivity Reagent kit on a LabChip GX (Perkin Elmer). Libraries were pooled and the pool was clustered at a concentration of 9 pmol on 2*8 lanes of paired-end sequencing high output flow cell (Illumina). Sequencing was performed for 2×125 cycles on a HiSeq 2500 with v4 SBS chemistry following Illumina's recommendations.

Image analysis and base calling were performed using the Illumina Real-Time Analysis. Raw data are available at (accession number #). Paired-end reads were mapped on the reference genome of zebrafish GRCz10 using STAR 2.4.0i (Dobin et al., Bioinformatics 2013 Jan 1; 29(1):15-21). Uniquely mapped reads were counted for each gene using the Python Package HTseq 0.9.1 (Anders et al., Bioinformatics. 2015 Jan. 15; 31(2):166-9) to determine the expression level of transcripts. Normalization of the read counts and differential expression analysis were performed using the Bioconductor 3.6 Package DESeq2 (Love et al., Genome Biol. 2014; 15(12):550). Genes with adjusted p-values smaller than 0.05 and log 2 fold-changes larger than 0.5 were used to compare genotype- and exercise-induced expression.

Gene ontology (GO) analysis was performed using DAVID Bioinformatics Resources 6.8 (Dennis et al., Genome Biol. 2003; 4(5):P3). KEGG pathway annotation was used for the enrichment test. Categories with p-value smaller than 0.05 were considered as significantly enriched.

Acute Oxidative Stress and Mitochondrial High-Resolution Respirometry

Adult AB zebrafish of 4-6 months old were exposed in water to acute oxidative stress with 3 μM Menadione (Sigma-Aldrich) incubation for 2 h at 28° C. Following the stress, fish were divided into controls and treatment groups. Controls of the oxidative stress were then incubated in clean water for 2 h at 28° C. Fish exposed to the glycine and glucose treatment were incubated in water containing the compound of interest for 2 h at 28° C. at the following doses: 50, 200, 450 μM (Sigma-Aldrich) for glycine; 500 μM and 5 mM (Sigma-Aldrich) for glucose; 450 μM for glycine, arginine and methionine (Sigma-Aldrich). Mitochondria crude extracts were prepared from fish trunk muscles as previously described, with minor changes (Frezza et al., Nat Protoc. 2007; 2(2):287-95). After BCA quantification of protein concentration, 150 μg of crude extract were used for high-resolution respirometry quantification. The Oxygraph-2k (O2k, OROBOROS Instruments) was used for measurements of respiration. Up to three O2k instruments (five chambers) were used in parallel. Experiments were performed at 28° C. in modified MiR05 (110 mM sucrose, 0.5 mM EGTA, 3 mM MgCl2, 20 mM taurine, 10 mM KH2PO4, 20 mM HEPES and 0.1% BSA essentially fatty acid free). Respiration of isolated mitochondria was determined using substrate-uncoupler-inhibitor titration (SUIT) protocols (Pesta and Gnaiger, Methods Mol Biol. 2012; 810:25-58) with modifications. Pyruvate, glutammate and malate (5 mM, 10 mM, 2 mM, respectively) were used as substrate to induce Complex I (CI) respiration in presence of ADP (1 mM). The addition of succinate (10 mM) in presence of ADP was used to induce Complex II (CII) respiration. CI respiration was calculated as the difference between total respiration (CI+CII) and the addition of CI inhibitor rotenone (0.5 μM); CII respiration was calculated as the difference between inhibited CI respiration and the addition of CII inhibitor malonic acid (5 mM). Total respiration (CI+CII, Tot resp) was assessed as the difference of the respiration in presence of all substrates and the total inhibition of CI and CII.

Results

PGC1a is the master regulator of mitochondrial biogenesis. We generated a zebrafish transgenic model that is overexpressing the PGC1a protein in muscle, which is leading to a massive production of mitochondria. Despite increased number of mitochondria is believed to be beneficial by increasing cellular energy availability, on the other hands it results in increased generation of ROS and oxidative stress which is exacerbated during aging (FIG. 1, protein carbonylation is a marker of oxidative damage).

Figure 2:
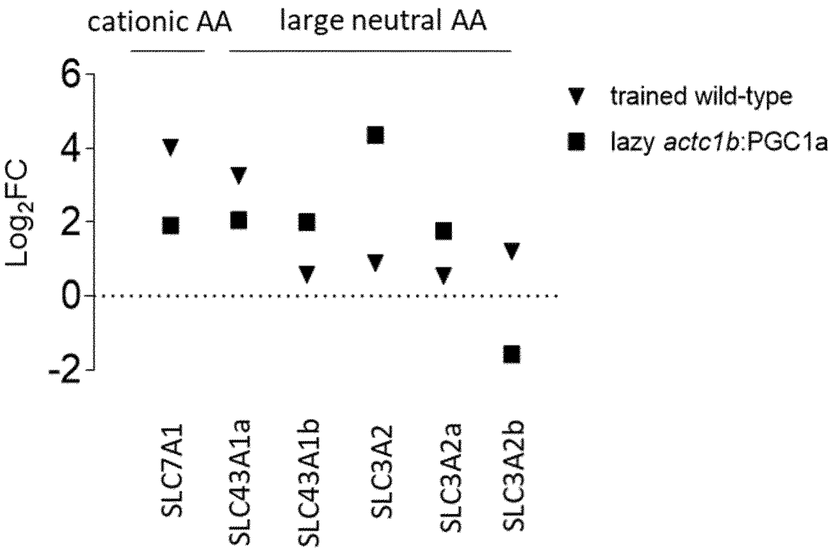
FIG. 2 is a graph showing PGC1A overexpression and exercise increase the expression of amino acids transporter, in particular related to transport of cationic amino acid (Arginine, Lysine, ornithine) and large neutral amino acid (leucine, Isoleucine, Valine, phenylalanine, Tyrosine, Tryptophan, Methionine, histidine). Results shown are Log2FC of differentially expressed genes in the comparison with lazy wild-type (n=8 per group).

We performed then gene expression analysis on young PGC1a fish and wild-type fish that were exercised ("trained wild type") in order to compare a more physiological model of induction of mitochondrial biogenesis with the genetic overexpression. We discovered that fish overproducing mitochondria increase pathways of catabolism of branched amino acids (Table 1) and amino acids transport in a similar way to fish undergoing chronic exercise, that increase mitochondria naturally (FIG. 2).

TABLE 1

Comparison between the enriched pathways expressed in PGC1α overexpression and exercise. Results of ranked gene set enrichment analysis are shown as table corresponding to adjusted p-values for each pathway.

| | actc1b:PGC1α | Trained wild-type |
|---|---|---|
| Valine, Leucine and isoleucine degradation | 1.83E−12 | 3.34E−09 |
| TCA cycle | 1.15E−09 | 6.02E−07 |
| Glycolysis/Gluconeogenesis | 0.00140529 | 5.02E−09 |
| Pyruvate metabolism | 0.00035729 | 5.66E−05 |
| Glyoxylate and dicarboxylate metabolism | 0.003502547 | 0.00124818 |
| Glycine, serine and threonine metabolism | 0.063820554 | 7.52E−08 |
| Synthesis and degradation of ketone bodies | 0.003107761 | 0.1201558 |

Figure 3:
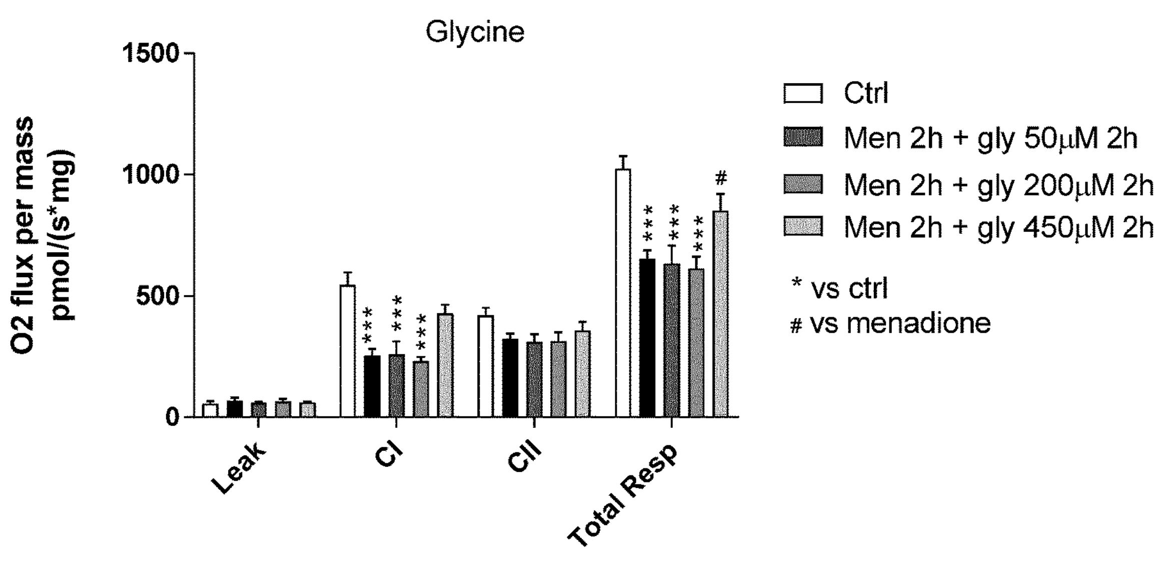
FIG. 3 is a graph showing that glycine is able to restore mitochondrial respiration in conditions of acute oxidative stress, but not glucose. Results represent the 02 consumption of isolated mitochondria from skeletal muscle of zebrafish (n=3 per condition). Statistics have been done using 2-way Anova with a Tukey multiple comparison test. *** p<0.001 #p<0.05.
Figure 3:
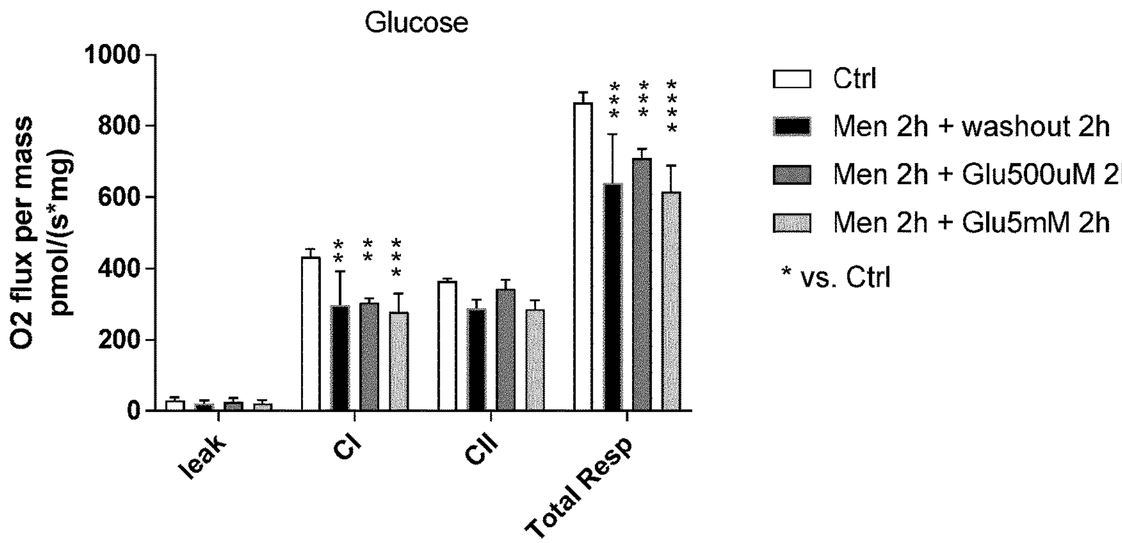
Figure 4:
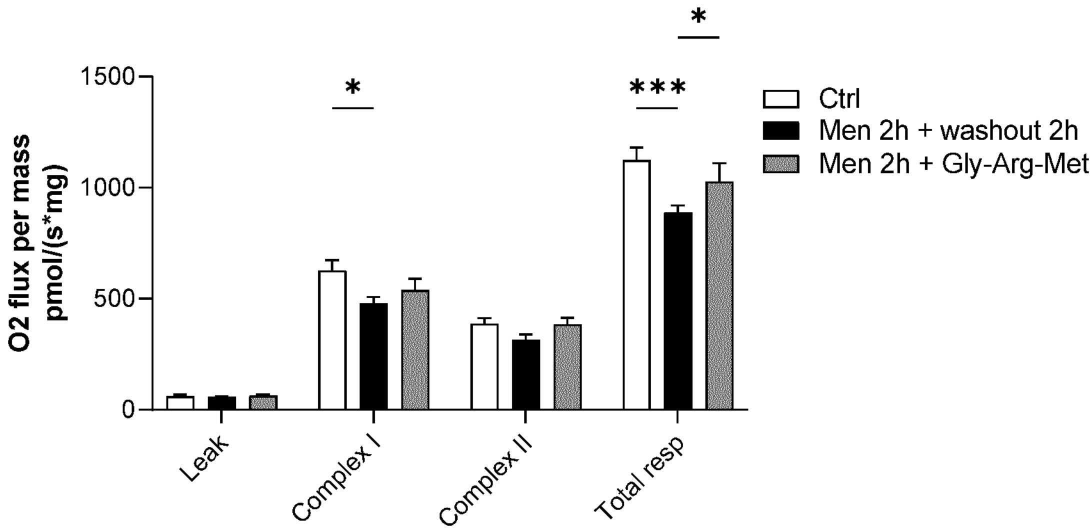
FIG. 4 is a graph showing the efficacy of a combination of glycine with arginine, representative of cationic amino acids, and methionine, representative of large neutral amino acids, on restoring mitochondrial respiration after acute oxidative stress. Results represent the 02 consumption of isolated mitochondria from skeletal muscle of zebrafish (n=7 for control and menadione control groups, n=8 for treatment with Gly-Arg-Met). Statistics have been done using 2-way Anova with a Tukey multiple comparison test. *** p<0.001 #p<0.05.

In particular, cationic amino acids transporter (SLC7A1) and large neutral amino acids transporters (SLC43A1a, SLC43A1b, SLC3A2, SLC3A2a, SLC3A2b) are overexpressed, suggesting a higher need of these amino acids to sustain mitochondrial function during high oxidative stress (FIG. 2). Moreover, we know from previous internal work that glycine is able to restore mitochondrial respiration after an acute oxidative stress. In FIG. 3, acute oxidative stress is induced with a short menadione treatment (Men) and this is decreasing Complex I dependent respiration. A treatment with glycine restores respiratory levels, while a treatment with glucose do not show any effects. Similarly, a treatment with a combination of glycine, arginine (as representative of cationic amino acids) and methionine (as representative as large neutral amino acids) has a beneficial effect in restoring O2 flux impaired by acute oxidative stress. These results support the hypothesis that oxidative stress reduces O2 flux in mitochondria due to the block of glycolytic enzymes; this block will reduce substrates availability for TCA cycle to support the respiratory chain. In these conditions, our data are suggesting that amino acids are used to feed TCA cycle and restore the energy imbalance.

These preliminary results will suggest that a combination of glycine with cationic and large neutral amino acids can help mitochondria to maintain a good functionality in conditions of high oxidative stress, such as aging, exercise, musculo-skeletal diseases, respiratory diseases, pain syndromes, neurodegenerative diseases or metabolic diseases.

It should be understood that various changes and modifications to the presently preferred embodiments described herein will be apparent to those skilled in the art. Such changes and modifications can be made without departing from the spirit and scope of the present subject matter and without diminishing its intended advantages. It is therefore intended that such changes and modifications be covered by the appended claims.

The invention claimed is:

1. A method for treating and/or preventing i) a mitochondria-related disease or condition associated with altered mitochondrial function and/or ii) at least one physical state selected from the group consisting of oxidative stress or a condition associated with oxidative stress in an individual in need thereof, the method comprising administering to the individual a composition comprising an effective amount of a combination of at least one glycine or functional derivative thereof selected from the group consisting of L-glycine, L-glycine ethyl ester, D-Allylglycine, N-[Bis(methylthio) methylene]glycine methyl ester, Boc-allyl-Gly-OH (dicyclohexylammonium) salt, Boc-D-Chg-OH, Boc-Chg-OH, (R)-N-Boc-(2'-chlorophenyl)glycine, Boc-L-cyclopropylglycine, Boc-L-cyclopropylglycine, (R)-N-Boc-4-fluorophenylglycine, Boc-D-propargylglycine, Boc-(S)-3-thienylglycine, Boc-(R)-3-thienylglycine, D-a-Cyclohexylglycine, L-a-Cyclopropylglycine, N-(2-fluorophenyl)-N-(methylsulfonyl)glycine, N-(4-fluorophenyl)-N-(methylsulfonyl)glycine, Fmoc-N-(2,4-dimethoxybenzyl)-Gly-OH, N-(2-Furoyl)glycine, L-a-Neopentylglycine, D-Propargylglycine, sarcosine, and Z-a-Phosphonoglycine trimethyl ester;

at least one large neutral amino acid selected from the group consisting of Leucine, Isoleucine, Valine, Phenylalanine, Tyrosine, Tryptophan, Threonine, and Methionine; and at least one cationic amino acid, wherein the mitochondria-related disease or condition is selected from the group consisting of stress, obesity, reduced metabolic rate, metabolic syndrome, cardiovascular disease, hyperlipidemia, respiratory diseases, pain syndromes, neurodegenerative disease, cognitive disorder, stress-induced or stress-related cognitive dysfunction, mood disorder, anxiety disorder, age-related neuronal death or dysfunction, musculo-skeletal disorder, sarcopenia, frailty, pre-frailty, chronic kidney disease, macular degeneration, and combinations thereof; and the at least one physical state is selected from the group consisting of deleterious effects of aging, muscle loss, metabolic syndrome, dyslipidemia, overweight, obesity, raised cholesterol levels, raised triglyceride levels, elevated fatty acid levels, fatty liver disease, renal disease, cardiovascular disease, musculo-skeletal diseases, respiratory diseases, pain syndromes, neurodegenerative disease, impaired cognitive function, myopathy, non-alcoholic steatohepatitis, tinnitus, dizziness, alcohol hangover, hearing impairment, osteoporosis, hypertension, atherosclerosis/coronary artery disease, myocardial damage after stress, traumatic brain injury, cystic fibrosis, inflammation, cancer, and HIV infection.

2. The method according to claim 1, wherein the at least one large neutral amino acid is Methionine.

3. The method according to claim 1, wherein the at least one cationic amino acid is selected from the group consisting of Arginine, Lysine and Ornithine.

4. The method according to claim 1, wherein the combination is administered orally.

5. The method according to claim 1, wherein the combination is administered in a composition selected from the group consisting of a food product, a food for special medical purposes (FSMP), a nutritional supplement, a dairy-based drink, a low-volume liquid supplement, a meal replacement beverage, and combinations thereof.

6. The method according to claim 1, wherein one or more of the at least one glycine or functional derivative thereof, the at least one large amino acid and/or at least one cationic amino acid are administered in the same composition.

7. The method according to claim 1, wherein one or more of the at least one glycine or functional derivative thereof and the at least one large amino acid and/or at least one cationic amino acid are administered in a different composition relative to the remainder of the combination.

8. A method for delaying off-set of metabolic decline, maintaining muscle mass, decreasing oxidative stress, maintaining immune function and/or maintaining cognitive function in a healthy adult in need thereof, the method comprising administering to the healthy adult a composition comprising an effective amount of a combination of at least one glycine or functional derivative thereof selected from the group consisting of L-glycine, L-glycine ethyl ester, D-Allylglycine, N-[Bis(methylthio) methylene]glycine methyl ester, Boc-allyl-Gly-OH (dicyclohexylammonium) salt, Boc-D-Chg-OH, Boc-Chg-OH, (R)-N-Boc-(2'-chlorophenyl)glycine, Boc-L-cyclopropylglycine, Boc-L-cyclopropylglycine, (R)-N-Boc-4-fluorophenylglycine, Boc-D-propargylglycine, Boc-(S)-3-thienylglycine, Boc-(R)-3-thienylglycine, D-a-Cyclohexylglycine, L-a-Cyclopropylglycine, N-(2-fluorophenyl)-N-(methylsulfonyl)glycine, N-(4-fluorophenyl)-N-(methylsulfonyl)glycine, Fmoc-N-(2,4-dimethoxybenzyl)-Gly-OH, N-(2-Furoyl)glycine, L-a-Neopentylglycine, D-Propargylglycine, sarcosine, and Z-a-Phosphonoglycine trimethyl ester;

at least one large neutral amino acid selected from the group consisting of Leucine, Isoleucine, Valine, Phenylalanine, Tyrosine, Tryptophan, Threonine, and Methionine; and at least one cationic amino acid.

9. A method according to claim 8, wherein the metabolic decline is fatty liver oxidative damage.

10. The method according to claim 8, wherein the healthy adult is elderly.

11. A method for i) mitigating deleterious effects of aging, ii) improving at least one of muscle performance or muscle recovery from exercise, exercise capacity and/or physical function, and/or iii) reducing severity of degenerative diseases in an individual in need thereof, the method comprising administering to the individual a composition comprising an effective amount of a combination of at least one glycine or functional derivative thereof selected from the group consisting of L-glycine, L-glycine ethyl ester, D-Allylglycine, N-[Bis(methylthio) methylene]glycine methyl ester, Boc-allyl-Gly-OH (dicyclohexylammonium) salt, Boc-D-Chg-OH, Boc-Chg-OH, (R)-N-Boc-(2'-chlorophenyl)glycine, Boc-L-cyclopropylglycine, Boc-L-cyclopropylglycine, (R)-N-Boc-4-fluorophenylglycine, Boc-D-propargylglycine, Boc-(S)-3-thienylglycine, Boc-(R)-3-thienylglycine, D-a-Cyclohexylglycine, L-a-Cyclopropylglycine, N-(2-fluorophenyl)-N-(methylsulfonyl)glycine, N-(4-fluorophenyl)-N-(methylsulfonyl)glycine, Fmoc-N-(2,4-dimethoxybenzyl)-Gly-OH, N-(2-Furoyl)glycine, L-a-Neopentylglycine, D-Propargylglycine, sarcosine, and Z-a-Phosphonoglycine trimethyl ester;

at least one large neutral amino acid selected from the group consisting of: Leucine, Isoleucine, Valine, Phenylalanine, Tyrosine, Tryptophan, Threonine, and Methionine; and at least one cationic amino acid.

12. The method according to claim 11, wherein the at least one cationic amino acid is selected from the group consisting of Arginine, Lysine and Ornithine.

13. The method according to claim 1, wherein the at least one large neutral amino acid is selected from the group consisting of Isoleucine, Valine, Phenylalanine, Tyrosine, Tryptophan, Threonine, and Methionine.

14. The method according to claim 1, wherein the at least one large neutral amino acid is selected from the group consisting of Leucine, Valine, Phenylalanine, Tyrosine, Tryptophan, Threonine, and Methionine.

15. The method according to claim 1, wherein the at least one large neutral amino acid is selected from the group consisting of Valine, Phenylalanine, Tyrosine, Tryptophan, Threonine, and Methionine.

16. The method according to claim 1, wherein the at least one large neutral amino acid is selected from the group consisting of Isoleucine, Tyrosine, Tryptophan, Threonine, and Methionine.

17. The method according to claim 1, wherein the composition comprises arginine and methionine.

18. The method according to claim 8, wherein the at least one cationic amino acid is selected from the group consisting of Arginine, Lysine and Ornithine.

19. The method according to claim 1, wherein the administering of the composition treats and/or prevents a mitochondria-related disease or condition associated with altered mitochondrial function in the individual, and the mitochondria-related disease or condition associated with altered mitochondrial function is selected from the group consisting of stress, obesity, reduced metabolic rate, metabolic syndrome, cardiovascular disease, hyperlipidemia, respiratory diseases, pain syndromes, neurodegenerative disease, cognitive disorder, stress-induced or stress-related cognitive dysfunction, mood disorder, anxiety disorder, age-related neuronal death or dysfunction, musculo-skeletal disorder, sarcopenia, frailty, pre-frailty, chronic kidney disease, macular degeneration, and combinations thereof.

20. The method according to claim 1, wherein the administering of the composition treats and/or prevents at least one physical state selected from the group consisting of oxidative stress or a condition associated with oxidative stress in the individual, and the at least one physical state is selected from the group consisting of deleterious effects of aging, muscle loss, metabolic syndrome, dyslipidemia, overweight, obesity, raised cholesterol levels, raised triglyceride levels, elevated fatty acid levels, fatty liver disease, renal disease, cardiovascular disease, musculo-skeletal diseases, respiratory diseases, pain syndromes, neurodegenerative disease, impaired cognitive function, myopathy, non-alcoholic steatohepatitis, tinnitus, dizziness, alcohol hangover, hearing impairment, osteoporosis, hypertension, atherosclerosis/coronary artery disease, myocardial damage after stress, traumatic brain injury, cystic fibrosis, inflammation, cancer, and HIV infection.

* * * * *